United States Patent
Le et al.

(10) Patent No.: US 10,881,664 B2
(45) Date of Patent: Jan. 5, 2021

(54) METHODS FOR TREATING EGFR MUTANT CANCERS

(71) Applicant: Novartis AG, Basel (CH)

(72) Inventors: NgocDiep Le, Potomac, MD (US); Gerald Lelais, San Diego, CA (US); Yong Jia, San Diego, CA (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 15/574,347

(22) PCT Filed: May 12, 2016

(86) PCT No.: PCT/IB2016/052751
§ 371 (c)(1),
(2) Date: Nov. 15, 2017

(87) PCT Pub. No.: WO2016/185333
PCT Pub. Date: Nov. 24, 2016

(65) Prior Publication Data
US 2018/0117059 A1    May 3, 2018

Related U.S. Application Data

(60) Provisional application No. 62/162,294, filed on May 15, 2015.

(51) Int. Cl.
*A61K 31/55*    (2006.01)
*A61P 35/00*    (2006.01)

(52) U.S. Cl.
CPC .............. *A61K 31/55* (2013.01); *A61P 35/00* (2018.01)

(58) Field of Classification Search
CPC ................................ A61K 31/55; A61P 35/00
See application file for complete search history.

(56) References Cited

FOREIGN PATENT DOCUMENTS

| WO | 2013184757 A1 | 12/2013 |
|----|---------------|---------|
| WO | 2016055916 A1 | 4/2016  |

OTHER PUBLICATIONS

Thress et al. Nat. Med., May 4, 2015, pp. 560-562.*
Oxnard et al. J. Thorac. Oncol., 2013, vol. 8, No. 2, pp. 179-184 or 1-12 as provided.*
Jia et al., "Abstract 1734: In vitro characterization of EGF816, a third-generation mutant-selective EGFR inhibitor", Cancer Research, 2014, vol. 74, No. 19, Proceedings: AACR Annual Meeting 2014.
Kasibhatla et al., "Abstract 1733: EGF816, a novel covalent inhibitor of mutant-selective epidermal growth factor receptor, overcomes T790M-mediated resistance in NSCLC", Cancer Research, 2014, vol. 74, issue 19, Proceedings: AACR Annual Meeting 2014.

\* cited by examiner

*Primary Examiner* — Samira J Jean-Louis
(74) *Attorney, Agent, or Firm* — David K. Cheung

(57) ABSTRACT

Methods for the treatment of EGFR mutated cancer. For example, treatment of non-small cell lung cancer (NSCLC) with activating EGFR mutations (e.g., L858R and ex19del) the acquired or resistant "gatekeeper" T790M mutation, or any combination of these mutations.

8 Claims, 3 Drawing Sheets

METHODS FOR TREATING EGFR MUTANT CANCERS

BACKGROUND OF THE INVENTION

Lung cancer is the most common cancer worldwide, with NSCLC accounting for approximately 85% of lung cancer cases. In Western countries, 10-15% non-small cell lung cancer (NSCLC) patients express epidermal growth factor receptor (EGFR) mutations in their tumors and Asian countries have reported rates as high as 30-40%. The predominant oncogenic EGFR mutations (L858R and ex19del) account for about 90% of EGFR NSCLC.

Besides the classic EGFR mutations (L858R and Ex19Del), EGFR Exon 20 insertion mutations (Ex20ins) were described to account for 4-10% of all EGFR mutations in patients, the third largest EGFR mutant patient population behind the classic (L858R and ex19del) EGFR mutations. EGFR Exon 20 insertion mutations include EGFR 20 duplication mutations.

EGFR-mutant patients are given an EFGR inhibitor as first line therapy. However, most patients develop acquired resistance, generally within 10 to 14 months. In up to 50% of NSCLC patients harboring a primary EGFR mutation treated with first generation reversible EGFR Tyrosine Kinase Inhibitors (TKIs), also referred to as first-generation TKIs, such as erlotinib, gefitinib and icotinib, a secondary "gatekeeper" T790M mutation develops.

Second-generation EGFR TKIs (such as afatinib and dacomitinib) have been developed to try to overcome this mechanism of resistance. These are irreversible agents that covalently bind to cysteine 797 at the EGFR ATP site. Second generation EGFR TKIs are potent on both activating [L858R, ex19del] and acquired T790M mutations in preclinical models. Their clinical efficacy has however proven to be limited, possibly due to severe adverse effects caused by concomitant wild-type (WT) EGFR inhibition.

This has led to the development of third-generation EGFR TKIs which are WT EGFR sparing. and also have relative equal potency for activating EGFR mutations [L858R, ex19del] and acquired T790M. Third generation EFGR TKIs such as AZD9291 (mereletinib, also known as osimertinib) and CO-1686 (rociletinib) are thus beginning to enter clinical development and to show significant initial promise (e.g., see "AZD9291 in EGFR Inhibitor-Resistant Non-Small-Cell Lung Cancer", Hanne et al, N Engl J Med, 2015; 372; 1689-99 and "Rociletinib in EGFR-Mutated Non-Small-Cell Lung Cancer", Sequist et al, N Engl J Med, 2015; 372; 1700-9). See also "ASP8273, a novel mutant-selective irreversible EGFR inhibitor, inhibits growth of non-small cell lung cancer (NSCLC) cells with EGFR activating and T790M resistance mutations", Sakagami et al, AACR; Cancer Res 2014; 74; 1728.

AZD9291, which may be administered in its methanesulfonate salt form, is also known as mereletinib or osimertinib, and is a compound of the structure

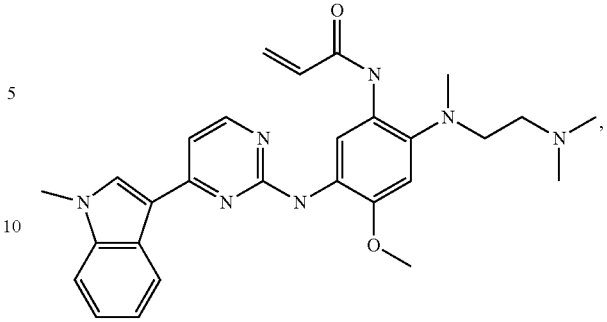

N-(2-[[2-(Dimethylamino)ethyl](methyl)amino]-4-methoxy-5-[[4-(1-methyl-1H-indol-3-yl)pyrimidin-2-yl]amino]phenyl)acrylamide which is described in PCT application WO 2013/014448. AZD9291 has been approved for the treatment of patients with metastatic epidermal growth factor receptor (EGFR) T790M mutation-positive non-small cell lung cancer (NSCLC), who have progressed on or after EGFR tyrosine kinase inhibitor (TKI) therapy.

CO-1686, which may be administered in its hydrobromide salt form, (rociletinib), N-(3-[[2-[[4-(4-Acetylpiperazin-1-yl)-2-methoxyphenyl]amino]-5-(trifluoromethyl)pyrimidin-4-yl]amino]phenyl)prop-2-enamide, is described in PCT application WO 2012/061299. Rociletinib has the following structure:

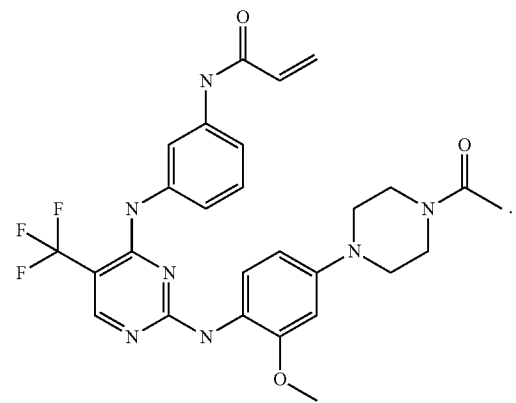 [SMILES: C=CC(=O)Nc1cccc(Nc2nc(Nc3ccc(N4CCN(C(C)=O)CC4)cc3OC)ncc2C(F)(F)F)c1]

Treatment with EGFR inhibitors has however not been shown to definitively translate into prolonged overall survival. Currently there is also no effective therapy available to target Ex20ins mutants, thus an unmet medical need exists. Hence there is still a need for additional treatment options for patients with EGFR mutant NSCLC.

SUMMARY OF THE INVENTION

The present invention relates to the use of (R,E)-N-(7-chloro-1-(1-(4-(dimethylamino)but-2-enoyl)azepan-3-yl)-1Hbenzo[d]imidazol-2-yl)-2-methylisonicotinamide (Compound A), or a pharmaceutically acceptable salt thereof. A particularly useful salt of Compound A is the mesylate salt thereof. WO2013/184757, the contents of which are hereby incorporated by reference, describes Compound A, its method of preparation and pharmaceutical compositions comprising Compound A. Compound A has the following structure:

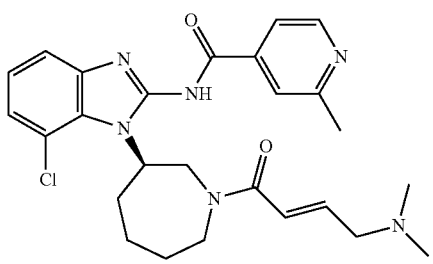 [SMILES: Cc1cc(C(=O)Nc2nc3cccc(Cl)c3n2[C@@H]2CCCCN(C(=O)/C=C/CN(C)C)C2)ccn1]

DESCRIPTION OF THE INVENTION

Figure 1:
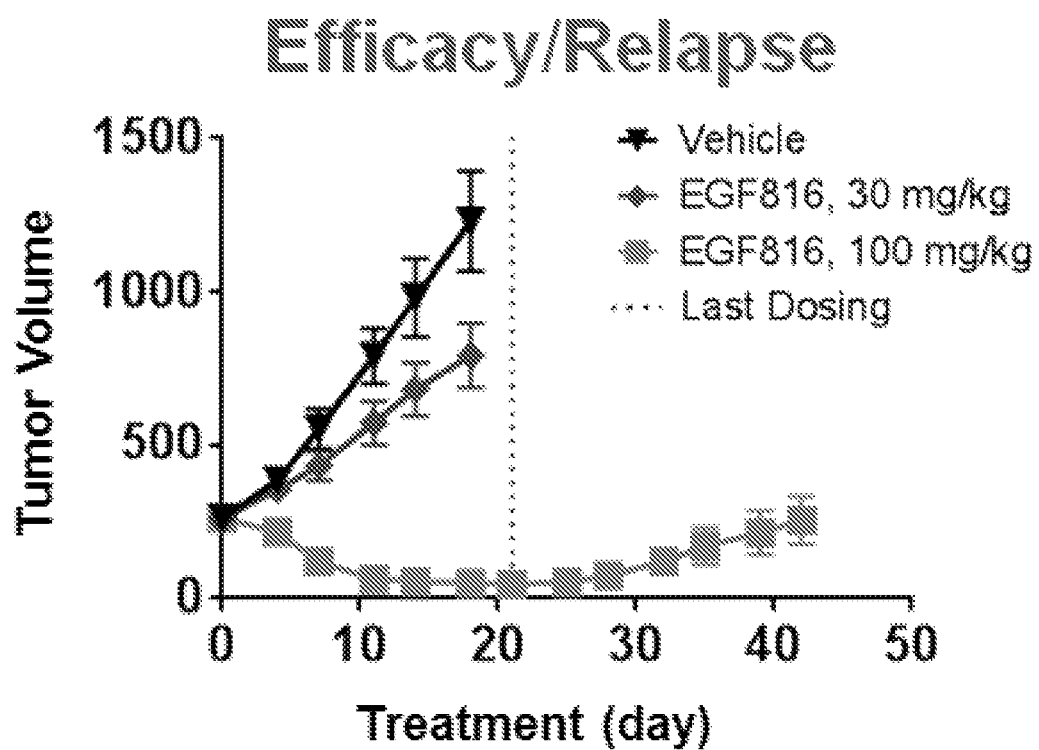
FIG. 1. Oral administration of Compound A (EGF816) once daily for 18 days resulted in tumor growth inhibition at 30 mg/kg, and significant tumor regressions (−81% on Day 18) were achieved at 100 mg/kg.

Compound A is a targeted covalent irreversible EGFR inhibitor that selectively inhibits activating and acquired resistance mutants (L858R, ex19del and T790M), while sparing WT EGFR. (see Jia et al, Cancer Res Oct. 1, 2014 74; 1734). Compound A has shown significant efficacy in EGFR mutant (L858R, ex19del and T790M) cancer models (in vitro and in vivo) with no indication of WT EGFR inhibition at clinically relevant efficacious concentrations. Compound A is also known as EGF816.

Compound A is a third-generation TKI (tyrosine kinase inhibitor).

Compound A demonstrated strong tumor regressions in several EGFR activating and resistant tumor models in vivo. These include HCC827 (ex19del), H3255 (L858R) and H1975 (L858R; T790M) that are representative of the relevant clinical settings. In all of the models Compound A inhibited tumor growth in a dose-dependent manner and achieved regressions of established tumors at well tolerated doses.

The HCC827 (ex19del activating mutation) mouse xenograft model was very sensitive to Compound A. Even at the lowest tested daily dose of 3 mg/kg, significant tumor regression was achieved. The effect was comparable to erlotinib at 60 mg/kg, a clinically relevant dose, which gave free plasma exposure similar to that observed at clinical efficacious dose. Compound A was very well tolerated, with no body weight loss observed up to 100 mg/kg, while erlotinib at 120 mg/kg showed significant body weight loss (~10%).

In the H3255 (L858R) mouse xenograft model, Compound A was tested at 30 mg/kg and demonstrated strong tumor regression with no effect on body weight compared to vehicle.

In the H1975 (L858R/T790M) mouse and rat xenograft models, significant tumor regression was achieved at doses≥30 mg/kg. Importantly, Compound A demonstrated much improved tolerability with superior efficacy as compared to second-generation irreversible pan-EGFR inhibitor afatinib.

In a PDX model of Ex20_H773_V774insNPH, Compound A demonstrated near complete regression at a tolerable dose with delayed outgrowth.

Together with the in vitro data, this indicates Compound A exhibits antitumor activity in the relevant patient-derived tumor cell lines at well tolerated doses and is predicted to have improved antitumor activity in humans with known EGFR-driven cancers.

Compared to the currently available EGFR inhibitors, Compound A is expected to improve/maintain efficacy on oncogenic EGFR mutant patients while having reduced side effects. Furthermore, Compound A has the potential to provide an effective therapy for T790M resistance patients, who have progressed on mereletinib and/or rociletinib.

It has surprisingly been found that despite sharing a similar mode of action, and similar minimal activity towards the WT EGFR inhibitor with other third-generation EFGR TKIs, Compound A may be beneficial to patients with tumors which are resistant to treatment with other third-generation EGFR TKIs (e.g AZD9291 and CO-1686). A therapeutic benefit of Compound A is that it may also show better tolerability in patients.

Compound A may therefore be beneficial to patients who have progressed on or after therapy with AZD9291.

In accordance with the above, the present invention therefore provides the following.

A method of treating NSCLC, including locally advanced or metastatic NSCLC, in a subject in need thereof, which comprises the step of:
administering a therapeutically effective amount of Compound A, or a pharmaceutically acceptable salt thereof, such as the mesylate salt thereof, to said subject and wherein the subject is determined to have a tumor which harbors an EGFR exon 20 insertion or deletion.

A method of treating NSCLC, including locally advanced or metastatic NSCLC, in a subject in need thereof, which comprises the step of:
administering a therapeutically effective amount of Compound A, or a pharmaceutically acceptable salt thereof, such as the mesylate salt thereof, to said subject and wherein the subject is determined to have a tumor which harbors an EGFR exon 20 insertion.

A method of treating NSCLC, including locally advanced or metastatic NSCLC, in a subject in need thereof, which comprises the step of:
administering a therapeutically effective amount of Compound A, or a pharmaceutically acceptable salt thereof, such as the mesylate salt, wherein the NSCLC tumor harbors an EGFR exon 20 insertion or deletion and wherein the tumor is resistant to gefitinib, erlotinib, neratinib, afatinib, PF00299804 (dacomitinib), mereletinib, or rociletinib and any combinations thereof.

A method of treating NSCLC, including locally advanced or metastatic NSCLC, in a subject in need thereof, which comprises the step of:
administering a therapeutically effective amount of Compound A, or a pharmaceutically acceptable salt thereof, such as the mesylate salt, wherein the NSCLC tumor harbors an EGFR exon 20 insertion or deletion and wherein the tumor is resistant to gefitinib, erlotinib, icotinib, neratinib, afatinib, PF00299804 (dacomitinib), mereletinib, ASP8273, HM61713, PF06747775 or rociletinib, and any combinations thereof.

A method of treating NSCLC, including locally advanced or metastatic NSCLC, in a subject in need thereof, which comprises the step of:
administering a therapeutically effective amount of Compound A, or a pharmaceutically acceptable salt thereof, such as the mesylate salt, wherein the subject is determined to have a tumor which harbors an EGFR exon 20 insertion or deletion and wherein the subject is no longer responding to therapy with gefitinib, erlotinib, neratinib, afatinib, PF00299804 (dacomitinib), mereletinib, or rociletinib and any combinations thereof.

A method of treating NSCLC, including locally advanced or metastatic NSCLC, in a subject in need thereof, which comprises the step of:
administering a therapeutically effective amount of Compound A, or a pharmaceutically acceptable salt thereof, such as the mesylate salt, wherein the subject is determined to have a tumor which harbors an EGFR exon 20 insertion or deletion and wherein the subject is no longer responding to therapy with gefitinib, erlotinib, neratinib, afatinib, PF00299804 (dacomitinib), mereletinib, ASP8273, HM61713, PF06747775 or rociletinib and any combinations thereof.

A method of treating NSCLC, including locally advanced or metastatic NSCLC, in a subject in need thereof, which comprises the step of:
administering a therapeutically effective amount of Compound A, or a pharmaceutically acceptable salt thereof, such as the mesylate salt, wherein the subject is determined to have a tumor which harbors an EGFR exon 20 insertion or deletion and wherein (a) the subject has progressed after therapy with gefitinib, erlotinib, neratinib, afatinib, PF00299804 (dacomitinib), mereletinib, or rociletinib and any combinations thereof; and/or (b) is intolerant to gefitinib, erlotinib, neratinib, afatinib, PF00299804 (dacomitinib), mereletinib, or rociletinib, and any combinations thereof.

A method of treating NSCLC, including locally advanced or metastatic NSCLC, in a subject in need thereof, which comprises the step of:
administering a therapeutically effective amount of Compound A, or a pharmaceutically acceptable salt thereof, such as the mesylate salt, wherein the subject is determined to have a tumor which harbors an EGFR exon 20 insertion or deletion and wherein (a) the subject has progressed after therapy with gefitinib, erlotinib, neratinib, afatinib, PF00299804 (dacomitinib), mereletinib, or rociletinib and any combinations thereof; and/or (b) is intolerant to gefitinib, erlotinib, neratinib, afatinib, PF00299804 (dacomitinib), mereletinib, ASP8273, HM61713, PF06747775 or rociletinib, and any combinations thereof.

A method of treating NSCLC, including locally advanced or metastatic NSCLC, in a subject in need thereof, which comprises the step of:
administering a pharmaceutical composition comprising Compound A, or a pharmaceutically acceptable salt thereof, such as the mesylate salt, wherein the subject is determined to have a tumor which harbors an EGFR exon 20 insertion or deletion and wherein (a) the subject has progressed after therapy with, mereletinib, and/or rociletinib; and/or
(b) the subject is intolerant to mereletinib and/or or rociletinib, and any combinations thereof.

A method of treating NSCLC, including locally advanced or metastatic NSCLC, in a subject in need thereof, which comprises the step of:
administering a pharmaceutical composition comprising Compound A, or a pharmaceutically acceptable salt thereof, such as the mesylate salt, wherein the subject is determined to have a tumor which harbors an EGFR exon 20 insertion or deletion and wherein (a) the subject has progressed after therapy with, mereletinib, ASP8273, HM61713, or PF06747775, and any combinations thereof; and/or
(b) the subject is intolerant to mereletinib, ASP8273, HM61713, PF06747775, and any combinations thereof.

A method of treating NSCLC, including locally advanced or metastatic NSCLC, in a subject in need thereof, which comprises step of:
administering a therapeutically effective amount of Compound A, or a pharmaceutically acceptable salt thereof, such as the mesylate salt, wherein the tumor harbors an EGFR exon 20 insertion or deletion and wherein the tumor is resistant to mereletinib, and/or rociletinib.

A method of treating NSCLC, including locally advanced or metastatic NSCLC, in a subject in need thereof, which comprises step of:
administering a therapeutically effective amount of Compound A, or a pharmaceutically acceptable salt thereof, such as the mesylate salt, wherein the tumor harbors an EGFR exon 20 insertion or deletion and wherein the tumor is resistant to mereletinib, and/or rociletinib.

A method of treating NSCLC, including locally advanced or metastatic NSCLC, in a subject in need thereof, which comprises the steps of: a. monitoring progression of NSCLC in a subject receiving treatment with gefitinib, erlotinib, neratinib, afatinib, PF00299804 (dacomitinib), mereletinib, or rociletinib and any combinations thereof, wherein progression of the NSCLC is indicative that said NSCLC is resistant to said treatment;
b. administering to the subject a pharmaceutical composition comprising Compound A, or a pharmaceutically acceptable salt thereof.

A method of treating NSCLC, including locally advanced or metastatic NSCLC, in a subject in need thereof, which comprises the steps of: (a). monitoring progression of NSCLC in a subject receiving treatment with gefitinib, erlotinib, neratinib, afatinib, PF00299804 (dacomitinib), mereletinib, ASP8273, HM61713, PF06747775 or rociletinib and any combinations thereof, wherein progression of the NSCLC is indicative that said NSCLC is resistant to said treatment;
(b). administering to the subject a pharmaceutical composition comprising Compound A, or a pharmaceutically acceptable salt thereof.

In accordance with the present disclosure, the following embodiments are also provided:

A method of treating NSCLC, including locally advanced or metastatic NSCLC, in a subject in need thereof, which comprises the step of:
administering a therapeutically effective amount of Compound A, or a pharmaceutically acceptable salt thereof, such as the mesylate salt thereof and wherein the subject is determined to have a tumor with a "de novo" EGFR T790M mutation.

A method of treating NSCLC, including locally advanced or metastatic NSCLC, in a subject in need thereof, which comprises the step of:
administering a therapeutically effective amount of Compound A, or a pharmaceutically acceptable salt thereof, such as the mesylate salt thereof, to said subject and wherein the subject is determined to have a tumor with EGFR activating mutations (e.g., L858R or ex19del) and an acquired T790M mutation and wherein the subject received treatment with a $1^{st}/2^{nd}$ generation EGFR TKI A method of treating NSCLC, including locally advanced or metastatic NSCLC, in a subject in need thereof, which comprises the step of:

administering a therapeutically effective amount of Compound A, or a pharmaceutically acceptable salt thereof, such as the mesylate salt, wherein the NSCLC tumor harbors EGFR activating mutations (e.g., L858R and/or ex19del) and an acquired EGFR T790M mutation and wherein the tumor is resistant to gefitinib, erlotinib, neratinib, afatinib, PF00299804 (dacomitinib), mereletinib, or rociletinib and any combinations thereof.

A method of treating NSCLC, including locally advanced or metastatic NSCLC, in a subject in need thereof, which comprises the step of:

administering a therapeutically effective amount of Compound A, or a pharmaceutically acceptable salt thereof, such as the mesylate salt, wherein the NSCLC tumor harbors EGFR activating mutations (e.g., L858R and/or ex19del) and an acquired EGFR T790M mutation and wherein the tumor is resistant to gefitinib, erlotinib, neratinib, afatinib, PF00299804 (dacomitinib), mereletinib, ASP8273, HM61713, PF06747775 or rociletinib and any combinations thereof.

A method of treating NSCLC, including locally advanced or metastatic NSCLC, in a subject in need thereof, which comprises the step of:

administering a therapeutically effective amount of Compound A, or a pharmaceutically acceptable salt thereof, such as the mesylate salt, wherein the subject is no longer responding to therapy with gefitinib, erlotinib, neratinib, afatinib, PF00299804 (dacomitinib), mereletinib, or rociletinib and any combinations thereof.

A method of treating NSCLC, including locally advanced or metastatic NSCLC, in a subject in need thereof, which comprises the step of:

administering a therapeutically effective amount of Compound A, or a pharmaceutically acceptable salt thereof, such as the mesylate salt, wherein the subject is no longer responding to therapy with gefitinib, erlotinib, neratinib, afatinib, PF00299804 (dacomitinib), mereletinib, ASP8273, HM61713, PF06747775 or rociletinib and any combinations thereof.

A method of treating NSCLC, including locally advanced or metastatic NSCLC, in a subject in need thereof, which comprises the step of:

administering a therapeutically effective amount of Compound A, or a pharmaceutically acceptable salt thereof, such as the mesylate salt, wherein the subject is no longer responding to therapy with, third generation EGFR TKIs (such as mereletinib and rociletinib, in particular, mereletinib).

A method of treating NSCLC, including locally advanced or metastatic NSCLC, in a subject in need thereof, which comprises the step of:

administering a therapeutically effective amount of Compound A, or a pharmaceutically acceptable salt thereof, such as the mesylate salt, wherein (a) the subject has progressed after therapy with first and/or second generation TKIs such as gefitinib, erlotinib, neratinib, afatinib, PF00299804 (dacomitinib), and any combinations thereof; and/or (b) has progressed on and/or is intolerant to third-generation TKIs such as mereletinib, or rociletinib, and any combinations thereof, in particular mereltinib.

A method of treating NSCLC, including locally advanced or metastatic NSCLC, in a subject in need thereof, which comprises the step of:

administering a pharmaceutical composition comprising Compound A, or a pharmaceutically acceptable salt thereof, such as the mesylate salt, to a subject with NSCLC, including locally advanced or metastatic NSCLC, wherein the subject is determined to have a tumor which harbors EGFR mutations (such as L858R, ex19del and T790M) and wherein (a) the subject has progressed after therapy with, mereletinib, and/or rociletinib, in particular merletinib; and/or (b) the subject is intolerant to mereletinib and/or or rociletinib, and any combinations thereof.

A method of treating NSCLC, including locally advanced or metastatic NSCLC, in a subject in need thereof, which comprises step of:

administering a therapeutically effective amount of Compound A, or a pharmaceutically acceptable salt thereof, such as the mesylate salt, to a subject with NSCLC, including locally advanced or metastatic NSCLC, wherein the tumor harbors EGFR mutations (such as L858R, ex19del and T790M) and wherein the tumor is resistant to mereletinib, and/or rociletinib, in particular merletinib.

A method of treating NSCLC, including locally advanced or metastatic NSCLC, in a subject in need thereof, which comprises the steps of:

a). monitoring progression of NSCLC in a subject receiving treatment with gefitinib, erlotinib, neratinib, afatinib, PF00299804 (dacomitinib), mereletinib, or rociletinib and any combinations thereof, wherein progression of the NSCLC is indicative that said NSCLC is resistant to said treatment;

b). administering to the subject a pharmaceutical composition comprising Compound A, or a pharmaceutically acceptable salt thereof.

The present invention is based on the finding that Compound A is particularly useful for subjects suffering NSCLC The present invention is based on the finding that Compound A is particularly useful for subjects suffering NSCLC, including locally advanced NSCLC or metastatic, with one or more of the following characteristics:

subjects who are intolerant to an approved EGFR TKI (e.g., erlotinib, gefitinib, afatinib) and/or for whom these drugs are not appropriate;

subjects who have progressed after therapy with an EGFR TKI other than Compound A;

subjects with a tumor exhibiting a "de novo" EGFR T790M mutation and who have not received prior treatment with an EGFR TKI (i.e. are treatment naïve with respect to an EGFR TKI);

subjects with a tumor harboring an EGFR exon 20 insertion or deletion; in particular, NSCLC harboring an exon 20 insertion subjects with tumors harboring EGFR activating mutation (e.g., L858R and/or ex19del) and without an acquired EGFR T790M mutation, and who have progressed on 1 prior treatment with a first-generation EGFR TKI (e.g., erlotinib, gefitinib or icotinib), or a second-generation EGFR TKI (e.g., afatinib or dacomitinib);

subjects with tumors harboring EGFR activating mutations (e.g., L858R or ex19del) and an acquired T790M mutation who have had treatment with a first- and or second-generation EGFR TKI and who have progressed on or are intolerant to a third-generation EGFR TKI (e.g., AZD9291, CO-1686, or ASP8273).

Throughout this disclosure, it is to be understood that NSCLC include advanced NSCLC or metastatic NSCLC. Advanced NSCLC refers to locally advanced or metastatic NSCLC. In advanced NSCLC, the NSCLC has spread to nearby tissue or to far away lymph modes.

Locally advanced NSCLC is defined as stage IIIB NSCLC not amenable to definitive multi-modality therapy including surgery.

Metastatic NSCLC refers to stage IV NSCLC. In metastatic NSCLC, the cancer has spread to other organs of the body.

EGFR mutation status may be determined by tests available in the art, e.g. QIAGEN Therascreen® EGFR test or other FDA approved tests. The therascreen EGFR RGQ PCR Kit is an FDA-approved, qualitative real-time PCR assay for the detection of specific mutations in the EGFR oncogene. Evidence of EGFR mutation can be obtained from existing local data and testing of tumor samples. EGFR mutation status may be determined from any available tumor tissue.

The terms "treat," "treating" or "treatment," as used herein, refers to methods of alleviating, abating or ameliorating a disease or condition symptoms, preventing additional symptoms, ameliorating or preventing the underlying metabolic causes of symptoms, inhibiting the disease or condition, arresting the development of the disease or condition, relieving the disease or condition, causing regression of the disease or condition, relieving a condition caused by the disease or condition, or stopping the symptoms of the disease or condition either prophylactically and/or therapeutically.

In addition, as used herein, the term "treat", "treating" or "treatment" of any disease or disorder, e.g. NSCLC, refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, the expression "first generation EGFR TKIs" includes erlotinib, gefitinib, icotinib and any combinations thereof.

As used herein, the expression "second generation EGFR TKIs" includes afatinib, dacomitinib and any combinations thereof.

As used herein, the expression "third generation EGFR TKIs" includes mereletinib, rociletinib and ASP8273, and any combinations thereof). Other examples of third generation EGFR TKIs include HM61713 and PF06747775. A more preferred third generation EGFR TKI is mereletinib (AZD9291).

A "de novo" T790M is defined as the presence of EGFR T790M mutation in NSCLC patients who have NOT been previously treated with any therapy known to inhibit EGFR.

To date, one NSCLC patient with a "de novo" T790M mutation has been enrolled in the Phase I part (dose-escalation) of this study. This patient has been treated with 225 mg of EGF816 and showed a tumor reduction of 41.54% from baseline and continued the study treatment for at least 5 months.

A subject suffering from cancer is defined as having progressed on, or no longer responding to therapy with one or more agents, or being intolerant to with one or more agents when the cancer he or she is suffering from, has progressed. The progression of cancer may be monitored by methods well known to those in the art. For example, the progression may be monitored by way of visual inspection of the cancer, such as, by means of X-ray, CT scan or MRI or by tumor biomarker detection. For example, an increased growth of the cancer indicates progression of the cancer. Progression of cancer such as NSCLC or tumors may be indicated by detection of new tumors or detection of metastasis or cessation of tumor shrinkage. Tumor evaluations can be made based on RECIST criteria (Therasse et al 2000), New Guidelines to Evaluate the Response to Treatment in Solid Tumors, Journal of National Cancer Institute, Vol. 92; 205-16 and revised RECIST guidelines (version 1.1) (Eisenhauer et al 2009) European Journal of Cancer; 45:228-247.

Tumor progression may be determined by comparison of tumor status between time points after treatment has commenced or by comparison of tumor status between a time point after treatment has commenced to a time point prior to initiation of the relevant treatment.

The terms "effective amount" or "therapeutically effective amount," as used herein, refer to a sufficient amount of a compound described herein being administered which will relieve to some extent one or more of the symptoms of the disease or condition being treated. An appropriate "effective" amount in any individual case may be determined using techniques, such as a dose escalation study. In connection with the administration of the drug, an "effective amount" indicates an amount that results in a beneficial effect for at least a statistically significant fraction of patients, such as a improvement of symptoms, a cure, a reduction in disease load, reduction in tumor mass or cell numbers, extension of life, improvement in quality of life, or other effect generally recognized as positive by medical doctors familiar with treating the particular type of disease or condition.

The dose of Compound A may be selected from a range of 50-250 mg, more preferably from a range of 50-150 mg. The dosages or doses quoted in the present disclosure refers to the amount present, in the drug product, of Compound A, calculated as the free base. The dosage may be 25, 50, 75, 100, 150, and 200 mg of Compound A. Preferably the dose is selected from 50, 75 and 100 mg of the drug substance referred to as its free base, as these doses may be better tolerated without loss of efficacy.

Compound A may be given at a dosage of 75, 100, 150, 200 and 225, 300 and 350 mg once daily. Preferably, Compound A may be given at a dosage of 50-150 mg once daily.

More preferably, Compound A may be given at a dosage of 50, 75, 100 mg or 150 mg once daily; more preferably, 50, 75 and 100 mg once daily.

Pharmaceutical compositions comprising Compound A, or a pharmaceutically acceptable salt thereof, are described in WO2013/184757. Compound A, or its pharmaceutically acceptable salt may be administered as an oral pharmaceutical composition in the form of a capsule formulation or a tablet.

The references cited throughout the application are incorporated herein by reference in their entirety.

EXAMPLES

Example 1. (R,E)-N-(7-chloro-1-(1-(4-(dimethylamino)but-2-enoyl)azepan-3-yl)-1H-benzo[d]imidazol-2-yl)-2-methylisonicotinamide (EGFRi) Biochemical Assays IC50 Determinations.
All EGFR biochemical assays were carried out as described in WO2013/184757.

Biological Results $IC_{50}$ determinations for Compound A obtained from a EGFR biochemical assay as described above from EGFR (L858R/T790M) without and with 90-minute pre-incubation were 0.008 µM and <0.001 µM, respectively.

Compound A shows an inhibition $IC_{50}$ determinations obtained from EGFR target modulation in engineered NIH/3T3 cell lines for L858R/T790M and L858R, 0.011 µM and 0.015 µM, respectively. For WT the value was 0.259 µM.

The $IC_{50}$ determinations obtained from EGFR target modulation in H1975 (EGFR L858/T790M), H3255 (EGFR L858R), and HEKn (EGFR WT) cell lines were 0.013 µM, 0.030 µM and 1.180 µM respectively.

Example 2—Mesylate Salt and Mesylate Form B (Mesylate Trihydrate Form) of Compound A (R,E)-N-(7-chloro-1-(1-(4-(dimethylamino)but-2-enoyl)azepan-3-yl)-1H-benzo[d]imidazol-2-yl)-2-methylisonicotinamide as obtained in Example 5 of WO2013/184757 (1.0 g) was dissolved in acetone (30 mL) by heating to 55° C. to form a solution. Methanesulfonic acid (325 µL) was added to acetone (50 mL), and the methanesulfonic acid/acetone (22.2 mL) was added to the solution at 0.05 ml/min. Following precipitation, the resulting suspension was cooled to room temperature at 0.5° C./min, and crystals were collected by filtration, and dried for 4 hours at 40° C. under vacuum. The collected crystals (300 mg) were suspended in acetone/$H_2O$ (6 mL; v/v=95/5) by heating to 50° C. The suspension was kept slurrying for 16 hours, and cooled to room temperature at 0.5° C./min. The crystal was collected by filtration and dried for 4 hours at 40° C. under vacuum.

The structure of (R,E)-N-(7-chloro-1-(1-(4-(dimethylamino)but-2-enoyl)azepan-3-yl)-1H-benzo[d]imidazol-2-yl)-2-methylisonicotinamide mesylate was confirmed by Differential Scanning Calorimetry, X-Ray Powder Diffraction, and Elemental Analyses. Melting point (170.1° C.). Theoretical calculated: % C (54.8); % H (5.9); % N (14.2); % O (13.5); % S (5.4); and % Cl (6.0); C:N ratio: 3.86. Found: % C (52.0); % H (5.8); % N (13.3); % Cl (5.9); C:N ratio: 3.91. Stoichiometry: 1.01.

In addition, crystalline mesylate form B was prepared by suspending 300 mg of crystalline mesylate form A in 6 mL of acetone/H2O (v/v=95/5) by heating to 50° C. The suspension was kept slurrying for 16 hours, and then the suspension was allowed to cool to room temperature at 0.5° C./min. The crystal was collected by filtration and afterwards dried for 4 hours at 40° C. under vacuum.

Example 3: Effect of Compound a (EGF816) on EGFR Exon 20 Insertion Models in In Vitro Cell Assays 3.1 Cell Lines NIH-3T3 Ex20_D770_N771insNPG cells (obtained from DFCI) were maintained in 10% FBS/DMEM P/S media supplemented with 2 µg/mL puromycin. Engineered BaF3 cells were maintained in 10% FBS/RMPI P/S media supplemented with 2 µg/mL puromycin. All cells were maintained in a humidified incubator at 37° C. with 5% $CO_2$.

Full-length, wild-type EGFR cDNA was sub-cloned into the cloning vector pCR4 (LifeTech) and used as a template to create Ex20ins mutants D770_N771insSVD and V769_D770insASV with a site-directed mutagenesis kit (Agilent). Sequence-verified clones were double-digested with endonucleases XhoI and HpaI and ligated to similarly digested pMSCVpuroLuc expression vector (in-house). HEK293T cells were co-transfected with mutant EGFR pMSCVpuroLuc vector and pEcoPak viral packaging vector. Supernatants containing viral vectors were subsequently used to infect IL-3 dependent BaF3 cells. Removal of IL-3 and addition of puromycin allowed for the final selection of pooled mutant EGFR-expressing BaF3 clones.

3.2 EGFR Target Modulation Assay

To assess compound efficacy on EGFR target modulation, phospho-EGFR was measured in NIH-3T3 Ex20_D770_N771insNPG cells treated with compound. These cells were plated overnight in 5% FBS/DMEM at 1000 cells/well (25 µL per well) in a 384-well tissue culture plate. Compounds from a 12-point dilution curve (20 µM highest final concentration, serial diluted by 3-fold in DMSO) were transferred to the cells using a 50 nL Pin Tool device and incubated in a humidified incubator at 37° C. with 5% $CO_2$ for 3 hours. Media was drained to 20 µL followed by the addition of 20 µL of 2×Lysis buffer with phosphatase and protease inhibitors. An aliquot of 25 µL was transferred to goat anti-EGFR capture antibody coated ELISA plates previously blocked with BSA. Active EGFR was detected with rabbit anti-phospho-EGFR (Y1173) followed by goat anti-rabbit IgG conjugated to HRP. Plates were developed with SuperSignal ELISA Pico chemiluminescent detection reagent and luminescence read on EnVision plate reader.

3.3 BaF3 Anti-Proliferation Assay

The anti-proliferative activity of compound A was assessed in two engineered BaF3 EGFR exon 20 insertion lines, Ex20_D770_N771insSVD and Ex20_V769_D770insASV. The cells were plated overnight in 10% FBS/RPMI P/S media at 500 cells per well (25 µL per well) in a 384-well tissue culture plate. Compounds from a 12-point dilution curve (20 µM highest final concentration, serial diluted by 3-fold in DMSO) were transferred to the cells using a 50 nL Pin Tool device and incubated in a humidified incubator at 37° C. with 5% $CO_2$ for 48 hours. After compound treatment, plates were developed with Bright-Glo™ Luciferase Assay System. Cell plates and Bright-Glo™ reagent were equilibrated to room temperature, and then 10 µL of Bright-Glo™ was added to each well. Plates were mixed by hand and allowed to incubate at room temperature for 5 minutes prior to measuring luminescence with EnVision plate reader.

3.4 Data Analysis

Raw data were uploaded to the LDDB server, and the $IC_{50}$ values for the compound in each cell line were calculated using non-linear curve fitting analysis.

3.5 Results

Compound A was tested in the target modulation assay of Ex20_D770_N771insNPG NIH-3T3 cell line, and proliferation assay of Ex20_D770_N771insSVD and Ex20_V769_D770insASV BaF3 cell lines. The representative $IC_{50}$ values for Compound A in Ex20_D770_N771insNPG, Ex20_D770_N771insSVD and Ex20_V769_D770insASV are 14, 7 and 11 nM, respectively, and are summarized in Table 1.

TABLE 1

IC$_{50}$ of Compound A (EGF816) on Ex20ins cell lines in target modulation and proliferation assays

| EGFR construct | Assay format | IC$_{50}$ (nM) |
| --- | --- | --- |
| Ex20_D770_N771insNPG | NIH-3T3 target modulation | 14 |
| Ex20_D770_N771insSVD | BaF3 proliferation | 7 |
| Ex20_V769_D770insASV | BaF3 proliferation | 11 |

As shown above, Compound A potently inhibits all three EGFR Ex20ins constructs with single to double digit nM potency. AZD9291 and CO-1686 were reported to be ineffective against the exon 20 insertion mutation (see "Discovery of a Mutant-Selective Covalent Inhibitor of EGFR that Overcomes T790M-Mediated Resistance in NSCLC", Walter et al, Cancer Discov. 2013; 3: 1404 and "AZD9291, an Irreversible EGFR TKI, Overcomes T790M-Mediated Resistance to EGFR Inhibitors in Lung Cancer: Cross et al. Cancer Discov. 2014; 4: 1046).

Example 4: Anti-Tumor Activity of Compound A in Subcutaneous PDX NSCLC Carcinoma Model LU0387 Harboring EGFR Ex20 H773 V774insNPH Mutation The in vivo efficacy and tolerability of EGF816 in subcutaneous PDX NSCLC carcinoma model LU0387 harboring EGFR Ex20_H773_V774insNPH mutation was investigated as follows.

Materials

BALB/c female nude mice (6-8 weeks; weighing approximately 18-22 g) were used as the experimental animal.

Formulation vehicle: 0.5% MC (methylcellulose) 0.5% Tween 80 in H$_2$O

Maintenance Conditions

An acclimation period of approximately one week was allowed between animal receipt and tumor inoculation in order to accustom the animals to the laboratory environment. The nude mice were maintained in a special pathogen-free environment and in micro isolator cages (5 mice per cage). All cages, bedding, and water were sterilized before use. The cages with food and water were changed twice a week. The targeted conditions for animal room environment and photoperiod were as follows:

| Temperature | 23 ± 3 C. |
| --- | --- |
| Humidity | 50 ± 20% |
| Light cycle | 12 hours light and 12 hours dark. |

All animals had free access to a standard certified commercial laboratory diet. Maximum allowable concentrations of contaminants in the diet were controlled and routinely analyzed by the manufacturers. Autoclaved municipal tap water, suitable for human consumption was available to the animals ad libitum. It is considered that there were no known contaminants in the dietary materials that could influence the tumor growth.

Establishment of LU0387 Subcutaneous Model

Tumor fragments from seed mice inoculated with selected primary human lung cancer tissues (LU0387) were harvested and used for inoculation into nude mice. Each mouse was inoculated subcutaneously at the right flank with one tumor fragment (2-3 mm in diameter) for tumor development. The treatments were started when mean tumor size reached ~262 mm$^3$. Each group consisted of 10 mice.

Before commencement of treatment, all animals were weighed and the tumor volumes were measured. Since the tumor volume can affect the effectiveness of any given treatment, mice were assigned into groups using randomized block design based upon their tumor volumes. This ensured that all the groups were comparable at the baseline.

Study Design

BALB/c female nude mice bearing the LU0387 tumors were randomized into 4 groups (n=10 mice per group) with an average tumor volume of 262 mm$^3$. EGF816 or AZD9291were formulated in 0.5% MC, 0.5% Tween80 suspension formulation and administered by oral gavage at a dosing volume of 10 μL/g of the animal body weight. Animals in each group received either vehicle or 30, 100 mg/kg EGF816 or 25 mg/kg AZD9291 once daily for 18 consecutive days, unless there was a tolerability issue, then a 2-day drug holiday was given. Tumor volumes and body weights of all animals were measured twice a week and were recorded throughout the study.

During the study, the care and use of animals were conducted in accordance with the regulations of the Association for Assessment and Accreditation of Laboratory Animal Care (AAALAC). Data analysis Measurement Tumor Volume and Body Weight Body weight was monitored twice a week and the % change in body weight was calculated as $(BW_{current}-BW_{initial})/(BW_{initial}) \times 100$. Data is presented as percent body weight change from the day of treatment initiation.

Tumor sizes were assessed twice a week. Tumor sizes were determined by using caliper measurements. Tumor volumes were calculated with the formula: (Length×Width× Width)/2.

Percent treatment/control (T/C) values for tumor were calculated using the following formula:

% T/C=100×ΔT/ΔC if ΔT>0%

Regression=100×ΔT/T$_{initial}$ if ΔT<0 where:

T=mean tumor volume of the drug-treated group on the final day of the study;

ΔT=mean tumor volume of the drug-treated group on the final day of the study−mean tumor volume of the drug-treated group on initial day of dosing;

T$_{initial}$=mean tumor volume of the drug-treated group on initial day of dosing;

C=mean tumor volume of the control group on the final day of the study; and

ΔC=mean tumor volume of the control group on the final day of the study−mean tumor volume of the control group on initial day of dosing.

All data are expressed as mean±standard error of the mean (SEM).

Statistical Analysis

Data were evaluated using one way ANOVA. All data were analyzed using SPSS 16.0. P<0.05 is considered to be statistically significant. Pharmacokinetic parameters were calculated by non-compartmental regression analysis.

Results

Method

The anti-tumor activity and tolerability of EGF816 and AZD9291 were examined in LU0387 mouse PDX model. Vehicle, EGF816 at a dose of 30, 100 mg/kg were orally administered once daily by oral gavage for 18 consecutive days. AZD9291 at 25 mg/kg was orally administered once daily for 10 consecutive days, a 2-day drug holiday was given due to tolerability issue, then dosing resumed on Day 13 until Day 18. At the end of the efficacy study on Day 18, 4/10 mice from EGF816 100 mg/kg group and AZD9291 25 mg/kg were continually dosed for another 3 days, and stopped post Day 21 dose, then the tumor re-growth was monitored.

Results

Oral administration of EGF816 at 30 mg/kg QD achieved 45% tumor inhibition. EGF816 at 100 mg/kg resulted in a tumor regression of 81% and achieved significant anti-tumor activity compared to vehicle (p<0.0001). AZD9291 at 25 mg/kg QD also achieved significant anti-tumor activity compared to the vehicle with a tumor regression of 26% (p<0.0001).

Tolerability of EGF816 and AZD9291 in LU0387 Mouse PDX Model

Figure 2:
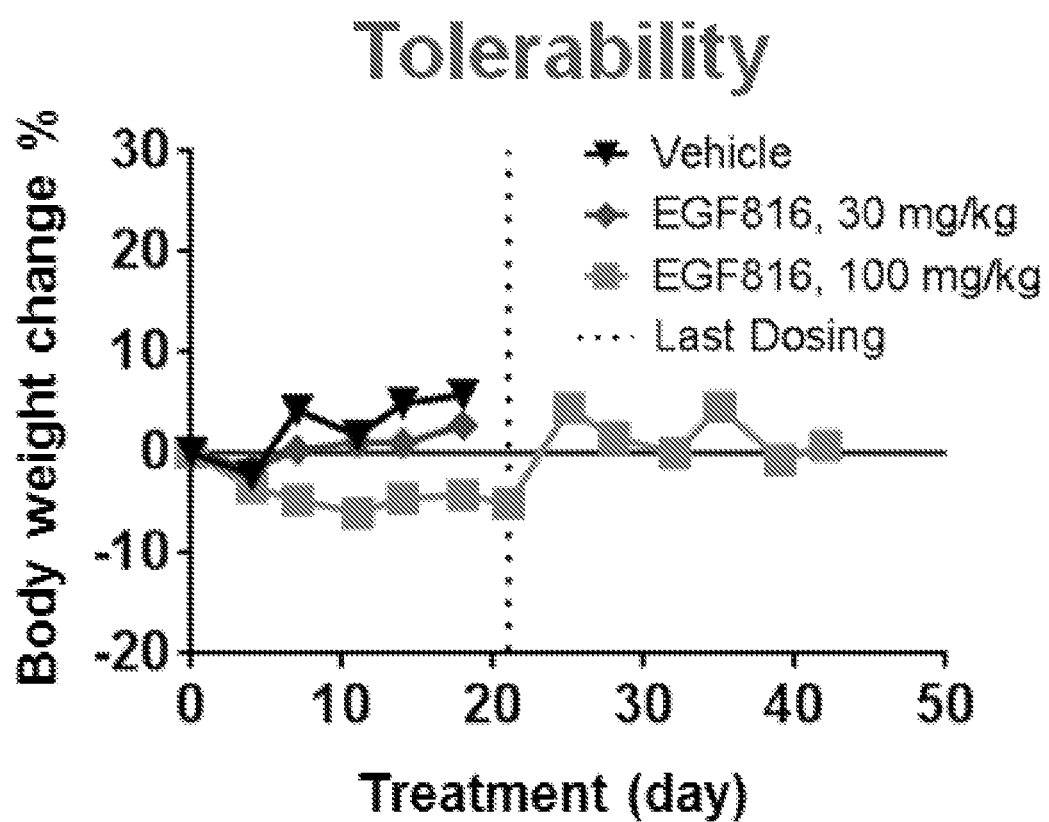
FIG. 2. The body weights of animals were monitored twice a week. EGF816 at both 30 and 100 mg/kg doses were well-tolerated. During the 18 day dosing, EGF816 at 30 mg/kg showed no body weight loss, while EGF816 at 100 mg/kg showed maximal body weight loss of ~4% compared to the control (FIG. 2).

The body weights of animals were monitored twice a week. EGF816 at both 30 and 100 mg/kg doses were well-tolerated. During the 18 day dosing, EGF816 at 30 mg/kg showed no body weight loss, while EGF816 at 100 mg/kg showed maximal body weight loss of ~4% compared to the control (FIG. 2). In contrary, AZD9291 at 25 mg/kg showed significant body weight loss on Day 11 (−13.2%), and a 2-day drug holiday had to be given on Day 11 due to this. However, after the drug holiday, the body weight recovered, and re-dosing of the drug was tolerated. The bodyweight changes on Day 14 and Day 18 for AZD9291 group were −4.7% and −6.9%, respectively.

Time to Relapse in LU0387 Mouse PDX Model Following 21 Days of Once Daily Oral Dosing of EGF816 and AZD9291

At the end of the efficacy study on Day 18, 4/10 mice in 100 mg/kg EGF816 and 25 mg/kg AZD9291 groups were continually dosed for another 3 days, then stopped post Day 21 dose. The tumor re-growth was monitored for these two groups.

After withdrawal of the drug treatment on day 21, tumors remained regressed for about a week before showing signs of tumor regrowth for EGF816 at 100 mg/kg group. In contrast, after withdrawal of AZD9291 (25 mg/kg) treatment, tumors regrew immediately.

Results

EGF816 (Compound A) was well-tolerated with little to no significant body weight loss associated at any of the doses tested during the entire treatment period. EGF816 achieved significant anti-tumor activity in LU0387 tumor bearing mice. Oral administration of EGF816 once daily for 18 days resulted in tumor growth inhibition at 30 mg/kg, and significant tumor regressions (−81% on Day 18) were achieved at 100 mg/kg. (FIG. 1) In comparison, EGFR clinical compound AZD9291, at 25 mg/kg was not well-tolerated and showed severe body weight loss. A 2-day drug holiday had to be given on Day 11. AZD9291 only achieved modest tumor regression (−26% on Day 18). Moreover, in the time to relapse study (4/10 mice at 100 mg/kg EGF816 and 25 mg/kg AZD9291 dose groups were post-monitored), upon cessation of EGF816 treatment on day 21, tumors stayed almost fully regressed for one additional week before showing slow tumor regrowth. In contrast, tumor regrowth was observed immediately after cessation of AZD9291 treatment on Day 21.

Overall, EGF816 demonstrated good efficacy and tolerability in this model (FIGS. 1 and 2).

Example 5: Modeling Binding Mode of Compound A

Figure 3:
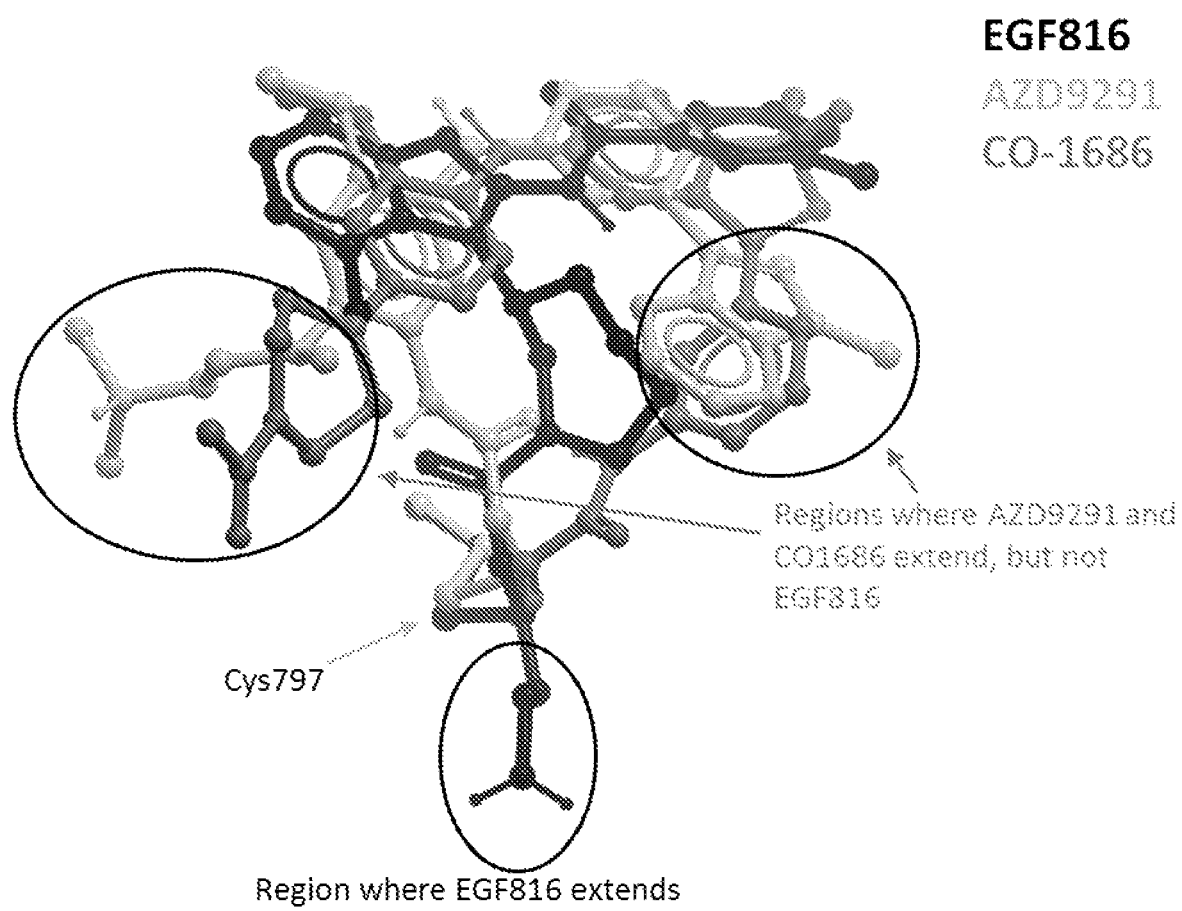
FIG. 3. Is a docking model of the spatial overlay of Compound A (i.e. EGF816), AZD9291 and CO-1686 binding to the EGFR kinase domain. The two upper circles in the spatial model show two regions where AZD9291 and CO1686 extend but EGF816 does not. The other lowest circle on the diagram shows a region below Cys797 where EGF816 extends but AZD9291 and CO1686 do not.

FIG. 3 shows a docking of the spatial overlay of Compound A (i.e. EGF816), AZD9291 and CO-1686 binding to the EGFR kinase domain. Modelling was carried out with Glide (Schrödinger, Inc., New York, N.Y.) using published WT and mutant co-crystal structures.

It can be seen that the spatial filling within the ATP-pocket is very much similar at the hinge region for the three compounds where the molecules are interacting through H-bonds with the protein backbone. However, there are unexpected differences in other regions of the molecule (highlighted by circles).

Thus patients with tumors which are resistant to treatment with AZD9291 or CO-1686 may be able to respond to treatment with Compound A. Additionally, the safety profile of EGF816 was seen to be different from other 3rd-generation EGFR TKIs; therefore, patients who are intolerant to treatment with those agents may be able to tolerate EGF816 treatment.

Therefore, based on the preclinical data and available clinical data for Compound A and the known clinical activity of other 3rd-generation EGFR inhibitors in advanced NSCLC patients harboring EGFR mutations, it is expected that Compound A would have significant antitumor activity in NSCLC patients harboring the activating EGFR mutations (e.g., L858R and ex19del) and/or the acquired/resistant "gatekeeper" T790M mutation. While sparing WT EGFR, Compound A is also expected to be better tolerated than currently available treatment options, including treatment with other third-generation TKIs such as AZD9291 or CO-1686. Taking into consideration of efficacy and safety, Compound A treatment should translate into longer sustained responses and improvement in patients' quality of life.

Example 6: Clinical Trial to Evaluate the Efficacy and Safety of Single-Agent Compound A in Adult Patients with Locally Advanced (Stage IIIB) or Metastatic (Stage IV) NSCLC Whose Tumors Harbor Specific EGFR Mutations Throughout this disclosure, advanced NSCLC refers to locally advanced or metastatic NSCLC. Locally advanced NSCLC is defined as stage IIIB NSCLC not amenable to definitive multi-modality therapy including surgery. Metastatic NSCLC refers to stage IV NSCLC.

A Phase I part (dose-escalation) of this study was carried out to determine the maximum tolerated dose (MTD) or recommended phase II dose (RP2D) and to evaluate the preliminary antitumor activity of single-agent EGF816 in adult patients with locally advanced (stage IIIB) or metastatic (stage IV) NSCLC harboring a documented EGFR T790M mutation.

A Phase II part of this study was carried out to evaluate the efficacy and safety of single-agent EGF816 in adult patients with locally advanced (stage IIIB) or metastatic (stage IV) NSCLC whose tumors harbor specific EGFR mutations. Patients were enrolled in six parallel groups as defined by the specific EGFR mutations and the number of prior lines of systemic antineoplastic therapies, including prior EGFR TKIs.

Group 1 patients are treatment naive patients, who have locally advanced or metastatic NSCLC with EGFR activating mutation (e.g., L858R and/or ex19del), have not received any systemic antineoplastic therapy for advanced NSCLC and are eligible to receive EGFR TKI treatment.

Group 2 patients are patients who have locally advanced or metastatic NSCLC with EGFR activating mutation AND an acquired T790M mutation (e.g., L858R and/or ex19del, T790M+) following progression on 1 and only 1 prior treatment with a 1st-generation EGFR TKI (e.g., erlotinib, gefitinib or icotinib) or 2nd-generation EGFR TKI (e.g., afatinib or dacomitinib).

Group 3 patients are patients who have locally advanced or metastatic NSCLC with a "de novo" T790M mutation (i.e. no prior treatment with any agent known to inhibit EGFR including EGFR TKI). Of note, one NSCLC patient with a "de novo" T790M mutation was enrolled in the Phase I part (dose-escalation) of this study. This patient was treated with 225 mg of EGF816 and showed a tumor reduction of 41.54% from baseline and continued the study treatment for at least 5 months.

Group 4 patients are patients who have locally advanced or metastatic NSCLC harboring EGFR exon 20 insertion or deletion. EGFR exon 20 insertion/deletions are resistant to clinically achievable doses of marketed or investigational EGFR inhibitors, such as gefitinib, erlotinib, neratinib, afatinib, and PF00299804 (dacomitinib) (Yasuda et al 2012). This group of patients currently represents a high unmet medical need.

Group 5 patients are patients who have locally advanced or metastatic NSCLC with EGFR activating mutation AND without an acquired T790M mutation (e.g., L858R and/or ex19del, T790M-) following progression on 1 and only 1 prior treatment with a 1st-generation EGFR TKI (e.g., erlotinib, gefitinib or icotinib) or 2nd-generation EGFR TKI (e.g., afatinib or dacomitinib).

Group 6 patients are patients who have locally advanced or metastatic NSCLC with EGFR activating mutation and an acquired T790M mutation (e.g., L858R or ex19del, T790M+) following progression on a prior treatment with a 1st/2nd-generation EGFR TKI, and have progressed on or are intolerant to a 3rd-generation EGFR TKI (e.g., AZD9291, CO-1686, or ASP8273).

Oral compound A was administered once daily on a continuous schedule until patient experiences unacceptable toxicity, progressive disease (PD), and/or treatment is discontinued at the discretion of the investigator, patient withdrawal of consent, or due to any other reasons.

The preliminary results from this study in advanced NSCLC patients with EGFR mutations (L858R and/or ex19del, T790M+) have shown a tolerable safety profile and significant antitumor activity of Compound A at different dose levels (75 mg, 150 mg, 225 mg and 350 mg) including the lowest dose tested, that is in line with other $3^{rd}$-generation EGFR TKIs such as AZD9291 and CO-1686. Preliminary efficacy results from 5 dose levels tested have showed an overall response rate (ORR) of 59.5% by Investigator assessment in 25 out of 42 evaluable patients.

Out of three patients with exon 20 insertion mutations who were treated with Compound A, two patients showed progressive disease at first evaluation and one patient had an unconfirmed partial response.

Based on the preclinical data for Compound A (EGF816) and the known clinical activity of other 3rd-generation EGFR inhibitors in advanced NSCLC patients harboring EGFR mutations, it is expected that Compound A would have significant antitumor activity in NSCLC patients harboring the activating EGFR mutations (e.g., L858R and ex19del) and/or the acquired/resistant "gatekeeper" T790M mutation. While sparing WT EGFR, EGF816 is also expected to be better tolerated than currently available treatment options. Taking into consideration of efficacy and safety, EGF816 treatment should translate into longer sustained responses and improvement in patients' quality of life.

The following Enumerated Embodiments are therefore provided.

ENUMERATED EMBODIMENTS

Enumerated Embodiment 1

A method of treating a cancer in a subject in need thereof, which comprises the step of:
administering a therapeutically effective amount of Compound A, or a pharmaceutically acceptable salt thereof, wherein the cancer is resistant to treatment with one or more third generation EGFR TKIs.

Enumerated Embodiment 2

A method according to Enumerated Embodiment 1, wherein the cancer is also resistant to treatment with first generation and/or second generation EGFR TKIs.

Enumerated Embodiment 3

A method of treating a cancer in a subject in need thereof, which comprises the step of:
administering a therapeutically effective amount of Compound A, or a pharmaceutically acceptable salt thereof, wherein the subject is progressing on or is no longer responding to therapy with one or more third generation EGFR TKIs.

Enumerated Embodiment 4

A method of treating a cancer in a subject in need thereof, which comprises the step of:
administering a therapeutically effective amount of Compound A, or a pharmaceutically acceptable salt thereof, wherein the subject is intolerant to therapy with one or more third generation EGFR TKIs.

Enumerated Embodiment 5

A method according to any one of the preceding Enumerated Embodiments where in the first generation EGFR TKIs is selected from erlotinib, gefitinib and icotinib.

Enumerated Embodiment 6

A method according to any one of the preceding Enumerated Embodiments where in the second generation EGFR TKIs is selected from afatinib or dacomitinib.

Enumerated Embodiment 7

A method according to any one of the preceding Enumerated Embodiments where in the third generation EGFR TKIs is selected from mereletinib, rociletinib and ASP8273.

Enumerated Embodiment 8

A method according to any one of the preceding Enumerated Embodiments wherein the cancer is NSCLC.

Enumerated Embodiment 9

A method according to Enumerated Embodiment 8 wherein the cancer is locally advanced or metastatic NSCLC.

Enumerated Embodiment 10

A method according to any one of the preceding Enumerated Embodiments wherein the pharmaceutically acceptable salt of Compound A is the mesylate salt.

Enumerated Embodiment 11

Compound A, or a pharmaceutically acceptable salt thereof, for use as first, second or third line treatment for NSCLC, e.g. advanced NSCLC or metastatic NSCLC.

Enumerated Embodiment 12

Compound A, or a pharmaceutically acceptable salt thereof, for use in a method of treating a cancer wherein the cancer is resistant to treatment with one or more third generation EGFR TKIs.

Enumerated Embodiment 13

Compound A, or a pharmaceutically acceptable salt thereof for use according to Enumerated Embodiment 12, wherein the cancer is additionally resistant to treatment with one or more second generation EGFR TKIs.

Enumerated Embodiment 14

Compound A, or a pharmaceutically acceptable salt thereof for use according to Enumerated Embodiment 12, in a method of treating a cancer wherein the cancer is additionally resistant to treatment with one or more first generation EGFR TKIs.

Enumerated Embodiment 15

Compound A, or a pharmaceutically acceptable salt thereof for use according to Enumerated Embodiment 12, in a method of treating a cancer wherein the cancer is additionally resistant to treatment with one or more first generation EGFR TKIs and additionally resistant to treatment with one or more second generation EGFR TKIs.

There are also provided the following embodiments.

EMBODIMENTS

Embodiment 1

A method of treating NSCLC in a patient, wherein the NSCLC harbors either an EGFR exon 20 insertion, the method comprising administering a therapeutically effective amount of Compound A, or a pharmaceutically acceptable salt thereof, to the patient
and wherein the patient has progressed on or after EGFR tyrosine kinase inhibitor (TKI) therapy with a third-generation TKI other than Compound A; or
wherein the patient is intolerant to EGFR tyrosine kinase inhibitor (TKI) therapy with a third-generation TKI other than Compound A.

Embodiment 2

A method of treating NSCLC in a patient, wherein the NSCLC harbors one or more EGFR activating mutations (e.g., L858R or ex19del), the method comprising administering a therapeutically effective amount of Compound A, or a pharmaceutically acceptable salt thereof, to the patient
and wherein the patient has progressed on or after EGFR tyrosine kinase inhibitor (TKI) therapy with a third-generation TKI other than Compound A; or
wherein the patient is intolerant to EGFR tyrosine kinase inhibitor (TKI) therapy with a third-generation TKI other than Compound A.

Embodiment 3

A method according to embodiment 2, wherein the NSCLC harbors L858R or ex19del activating mutation.

Embodiment 4

A method according to embodiment 3, wherein the NSCLC further harbors an acquired T790M mutation.

Embodiment 5

A method according to any one of the preceding embodiments, wherein the third-generation TKI is osimertinib (mereletinib), rociletinib, ASP8273, HM61713 or PF06747775.

Embodiment 6

A method according to embodiment 5, wherein the third-generation TKI is osimertinib (mereletinib).

Embodiment 7

A method according to any one of the preceding embodiments, wherein the patient has received prior treatment with one or more first and/or one or more second generation TKIs and has progressed on or after such therapy.

Embodiment 8

A method according to embodiment 7, wherein the first generation TKI is erlotinib, gefitinib or icotinib.

Embodiment 9

A method according to embodiment 7 or 8, wherein the second generation TKI is afatinib or dacomitinib.

Embodiment 10

A method according to any one of the preceding enumerated embodiments wherein the NSCLC is locally advanced or metastatic NSCLC.

Embodiment 11

A method of treating advanced or metastatic NSCLC exhibiting a de novo EGFR T790M mutation in a patient, the method comprising administering a therapeutically effective amount of Compound A, or a pharmaceutically acceptable salt thereof, to the patient, and wherein the patient has not received any prior treatment with an EGFR TKI.

Embodiment 12

A method of treating advanced or metastatic NSCLC harboring an EGFR exon 20 insertion in a patient, the method comprising administering a therapeutically effective amount of Compound A, or a pharmaceutically acceptable salt thereof, to the patient.

Embodiment 13

A method according to any one of the preceding embodiments wherein Compound A is administered in a dose ranging from 50-250 mg.

Embodiment 14

A method according to embodiment 13, wherein Compound A is administered once daily.

Embodiment 15

Compound A, or a pharmaceutically acceptable salt thereof, for use in a method of treating advanced or metastatic NSCLC in a patient, wherein the NSCLC harbors an EGFR exon 20 insertion.

Embodiment 16

Compound A, or a pharmaceutically acceptable salt thereof, for use in a method of treating NSCLC in a patient, wherein the NSCLC harbors an EGFR exon 20 insertion or
wherein the NSCLC harbors one or more EGFR activating mutations (e.g., L858R or ex19del),
and wherein the patient has progressed on or after EGFR tyrosine kinase inhibitor (TKI) therapy with a third-generation TKI other than Compound A.

The invention claimed is:

1. A method of treating NSCLC in a patient comprising administering to the patient a therapeutically effective amount of (R,E)-N-(7-chloro-1-(1-(4-(dimethylamino)but-2-enoyl)azepan-3-yl)-1Hbenzo[d]imidazol-2-yl)-2-methylisonicotinamide (Compound A), or a pharmaceutically acceptable salt thereof,
wherein the NSCLC harbors an EGFR exon 20 insertion, and wherein Compound A is administered in a dose ranging from 75 mg to 225 mg daily.

2. The method according to claim 1, wherein the NSCLC further harbors an L858R activating mutation or an ex19del EGFR activating mutation.

3. The method according to claim 2, wherein the NSCLC further harbors an acquired T790M mutation.

4. The method according to claim 1, wherein the patient has received prior treatment with (i) one or more first-generation TKIs, and/or (ii) one or more second-generation TKIs;
and the patient has progressed on or after such therapy.

5. The method according to claim 4, wherein the first generation TKI is erlotinib, gefitinib or icotinib.

6. The method according to claim 5, wherein the second generation TKI is afatinib or dacomitinib.

7. The method according to claim 6, wherein the NSCLC is locally advanced or metastatic NSCLC.

8. The method according to claim 1, wherein Compound A is administered at a dose of 150 mg once daily.

* * * * *